United States Patent
Hsieh et al.

(10) Patent No.: US 9,731,312 B2
(45) Date of Patent: Aug. 15, 2017

(54) NEBULIZATION STRUCTURE

(71) Applicant: MICRO BASE TECHNOLOGY CORPORATION, Bade, Taoyuan County (TW)

(72) Inventors: Shu-Pin Hsieh, Bade (TW); Tun-Ying Fang, Bade (TW); Mei-Hui Huang, Bade (TW); Yu-Ju Su, Bade (TW); Chin-Jung Chang, Bade (TW)

( * ) Notice: Subject to any disclaimer, the term of this patent is extended or adjusted under 35 U.S.C. 154(b) by 694 days.

(21) Appl. No.: 13/669,424

(22) Filed: Nov. 5, 2012

(65) Prior Publication Data

US 2013/0112770 A1   May 9, 2013

(30) Foreign Application Priority Data

Nov. 8, 2011   (TW) .............................. 100221054 U (51) Int. Cl.
| | |
|---|---|
| *B05B 17/06* | (2006.01) |
| *A61M 11/00* | (2006.01) |
| *A61M 15/00* | (2006.01) |
| *B05B 17/00* | (2006.01) |
| *F02M 61/18* | (2006.01) |
| *A01M 1/20* | (2006.01) |

(52) U.S. Cl.
CPC ....... *B05B 17/0661* (2013.01); *A61M 11/005* (2013.01); *A61M 15/0085* (2013.01); *B05B 17/0638* (2013.01); *B05B 17/0646* (2013.01); *A01M 1/205* (2013.01); *F02M 61/186* (2013.01)

(58) Field of Classification Search
CPC ............ B05B 17/0638; B05B 17/0646; F02M 61/186; A61M 11/005; A61M 15/0085; A01M 1/205
USPC .................................. 239/102.1, 102.2, 601
See application file for complete search history.

(56) References Cited

U.S. PATENT DOCUMENTS

| | | | | |
|---|---|---|---|---|
| 5,152,456 | A * | 10/1992 | Ross ................. | A61M 15/0085 128/200.16 |
| 6,901,926 | B2 * | 6/2005 | Yamamoto ........ | A61M 15/0085 128/200.16 |
| 7,093,776 | B2 * | 8/2006 | Schneider ............ | F02M 61/186 239/494 |
| 2003/0121999 | A1 * | 7/2003 | Huebel .............. | F02M 51/0671 239/585.1 |
| 2005/0284965 | A1 * | 12/2005 | Schneider ............ | F02M 61/186 239/533.12 |
| 2006/0097068 | A1 * | 5/2006 | Urich .................. | A61M 11/005 239/102.1 |
| 2006/0243820 | A1 * | 11/2006 | Ng ...................... | B05B 17/0646 239/102.1 |

(Continued)

*Primary Examiner* — Alexander Valvis
(74) *Attorney, Agent, or Firm* — Opes IP Consulting Co. Ltd.

(57) ABSTRACT

A nebulization structure includes a driving element, a structure plate and a nebulization plate. The structure plate is installed on a side of the driving element, and the structure plate is substantially in a circular disc shape and has a plurality of through holes, and at least one rib is formed between adjacent through holes to define a water guide passage. The nebulization plate is clamped between the driving element and the structure plate and made of a polymer material to overcome the problems of having easy metal fatigue and embrittlement of the nebulization plate made of metal, and being corroded by corrosive liquids.

13 Claims, 14 Drawing Sheets

(56) References Cited

U.S. PATENT DOCUMENTS

| | | | | |
|---|---|---|---|---|
| 2006/0289673 A1* | 12/2006 | Wang | ............... | B05B 17/0646 239/102.1 |
| 2008/0073447 A1* | 3/2008 | Wang | ............... | B05B 17/0646 239/302 |
| 2011/0290910 A1* | 12/2011 | Feriani | ............. | B05B 17/0638 239/102.1 |

* cited by examiner

NEBULIZATION STRUCTURE

CROSS-REFERENCE TO RELATED APPLICATIONS

This non-provisional application claims priority under 35 U.S.C. §119(a) on Patent Application No(s). 100221054 filed in Taiwan, R.O.C. on Nov. 8, 2011, the entire contents of which are hereby incorporated by reference.

BACKGROUND OF THE INVENTION

1. Field of the Invention

The present invention relates to a nebulization structure, in particular to the nebulization structure that uses a nebulization plate and a piezoelectric annular plate in a nebulization process.

2. Description of the Related Art

As science and technology advance and consumers have increasing higher requirements on a light, thin, short and compact design of various different products, different technical areas including medicine, bio-tech, computer technology, printing or energy industry tend to develop products with a fine and miniaturized design.

Figure 1:
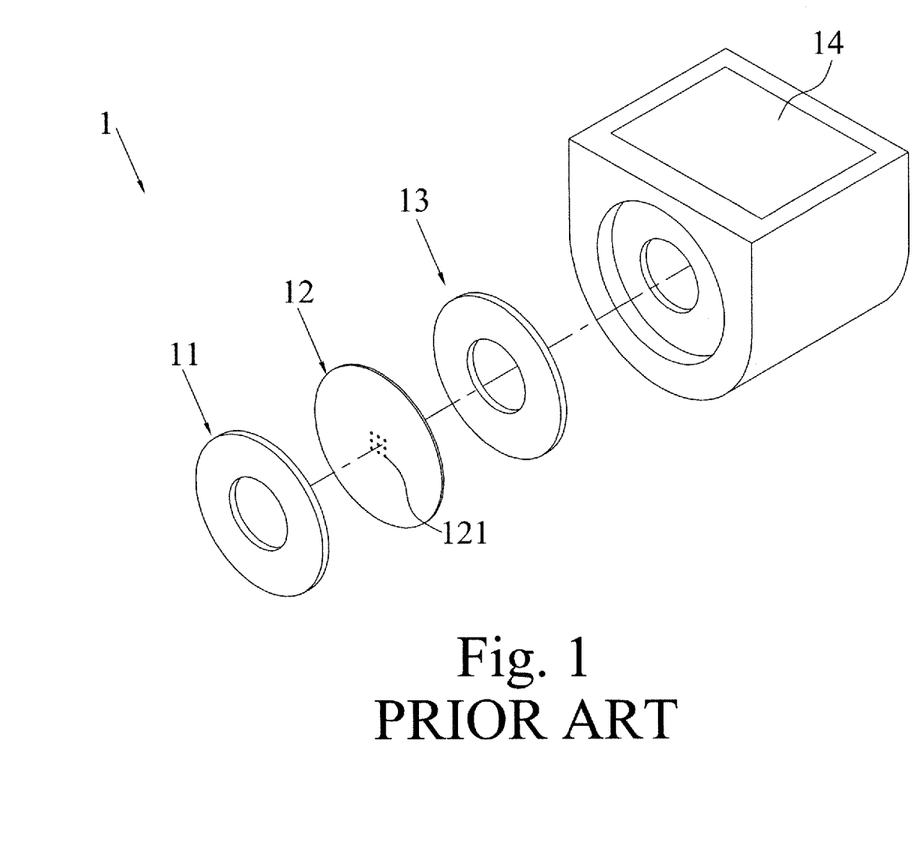
FIG. 1 is an exploded view of a conventional nebulization structure.
Figure 2:
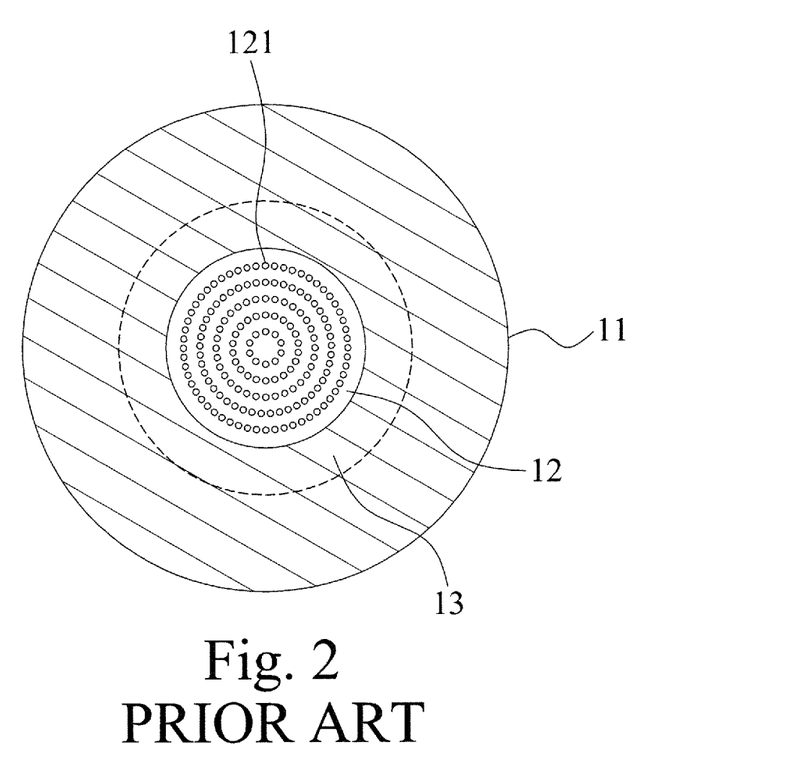
FIG. 2 is a perspective view of a conventional nebulization structure.
Figure 3:
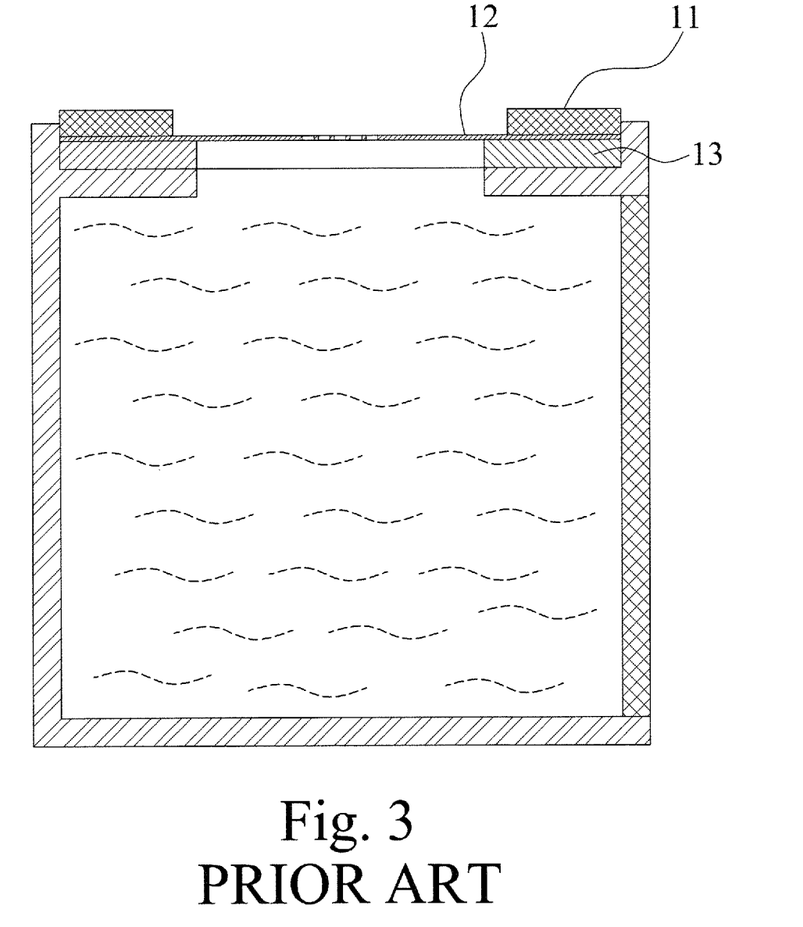
FIG. 3 is a cross-sectional view of a conventional nebulization structure.

With reference to FIGS. 1, 2 and 3 for an exploded view, a perspective view and a cross-sectional view of a conventional nebulization structure respectively, the nebulization structure 1 is installed on a side of a cavity 14 and comprises a piezoelectric annular plate 11, a nebulization plate 12 and a structure annular plate 13. Wherein, both sides of the nebulization plate 12 are packaged and fixed between the piezoelectric annular plate 11 and the structure annular plate 13. The structure annular plate 13 is provided for fixing the nebulization plate 12 and oscillated by the piezoelectric annular plate 11 to vibrate together with the piezoelectric annular plate 11.

When an electric field is applied to the piezoelectric annular plate 11 from the lateral side of the piezoelectric annular plate 11, the piezoelectric annular plate 11 produces a transverse contraction and induces the deformation of the nebulization plate 12 to link the nebulization plate 12 and deform accordingly. Since the piezoelectric contraction produced by the piezoelectric annular plate 11 and the deformation of the nebulization plate 12 vary, the nebulization plate 12 of nebulization structure 1 is induced a curved movement to produce up and down oscillations of the nebulization plate 12.

When the operating frequency of the piezoelectric annular plate 11 is exactly equal to the vibration frequency of the overall structure, spray holes 121 formed on the nebulization plate 12 produce a very high speed of a spray, so that the inertia force of droplets formed on the spray holes 121 of the nebulization plate 12 is greater than the surface tension of the spray holes to spray micro droplets from the spray holes in order to achieve a fluid nebulization effect.

Since metal has a better effect of transmitting the vibration energy, the conventional nebulization plate 12 is generally made of a metal material. Due to the limitation of the metal material, the metal nebulization plate 12 may become fatigued, embrittled, or gradually weaken in the oscillation effect easily to result in cracking the nebulization plate 12, after the nebulization plate 12 has been operated at a high frequency oscillation for a long time.

If the nebulization plate 12 is made of a polymer material instead, the drawbacks of the metal nebulization plate 12 can be overcome, but the polymer material has a loosened structural arrangement of molecules and an insufficient rigidity, the efficiency for the nebulization plate to receive the energy transmitted from the piezoelectric driving element becomes too low, so that the nebulization plate fails to transmit the vibration energy and results in a poor nebulization effect.

In addition, the conventional structure annular plate 13 is an annular structure, so that when it is combined with the piezoelectric annular plate 11 and the nebulization plate 12 to form a nebulization structure, most of the vibration energy produced by the piezoelectric annular plate 11 can only be transmitted to the nebulization plate 12 which is relative to the inner side of the structure annular plate 13, and thus causing the vibration energy failing to be transmitted to the center position of the nebulization plate 12 effectively. As a result, the center position of the nebulization plate 12 cannot be oscillated effectively, and the nebulization effect becomes low.

SUMMARY OF THE INVENTION

Therefore, it is a primary objective of the present invention to provide a nebulization structure, particularly the nebulization structure that is applicable to corrosive liquids and has a nebulization plate capable of producing vibration energy up to a level that can achieve the expected nebulization effect.

To achieve the aforementioned objective, the present invention provides a nebulization structure comprising a driving element, a structure plate and a nebulization plate. The structure plate is installed on a side of the driving element, and the structure plate is in a circular disc shape and has a plurality of through holes, and at least one rib formed between two adjacent through holes. The nebulization plate is clamped between the driving element and the structure plate.

Wherein, the through holes are arranged radially into a circular shape with respect to the center position of the structure plate.

Wherein, the driving element is a piezoelectric annular plate.

Wherein, the structure plate further includes a plurality of glue overflow passages, each formed at the external periphery of each respective through hole and at a position corresponding to the internal periphery of the piezoelectric annular plate.

Wherein, the nebulization plate and the structure plate are coupled and combined by an adhesive.

Wherein, the nebulization plate is made of a polymer material or a metal material.

Wherein, if the nebulization plate is made of a polymer material, the polymer material is polyimide, polyethylene (PE), polypropylene (PP) or polyether ether ketone (PEEK).

Wherein, the structure plate is made of a metal material or a polymer material.

Wherein, if the structure plate is made of a polymer material, the polymer material is polyimide, polyethylene (PE), polypropylene (PP) or polyether ether ketone (PEEK).

Wherein, if there are three or four through holes, each through hole is arranged radially into a circular shape with respect to the center position of the structure plate.

Wherein, if there are four through holes, one of the four through holes is formed at the center position of the structure plate and the other three through holes are arranged radially into a circular shape with respect to the center position of the structure plate.

Wherein, if there are five through holes, one of the five through holes is formed at the center position of the structure plate and the other four through holes are arranged radially into a circular shape with respect to the center position of the structure plate.

DETAILED DESCRIPTION OF THE PREFERRED EMBODIMENTS

The technical content of the present invention will become apparent with the detailed description of preferred embodiments and the illustration of related drawings as follows.

Figure 4:
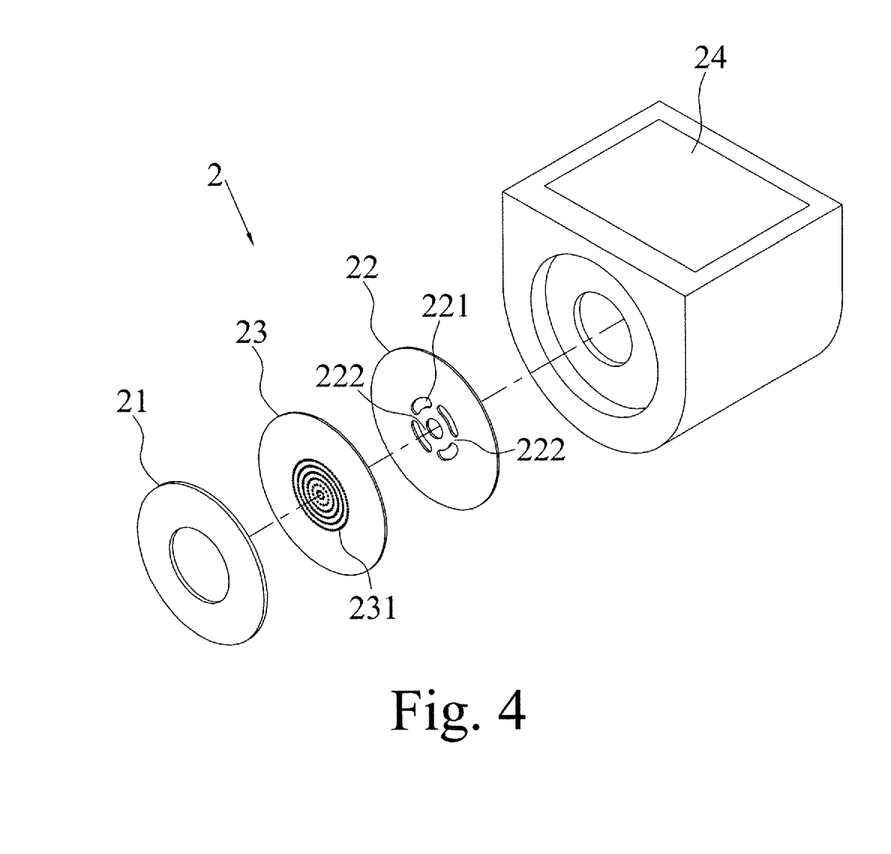
FIG. 4 is a perspective view of a nebulization structure in accordance with a first preferred embodiment of the present invention.
Figure 5:
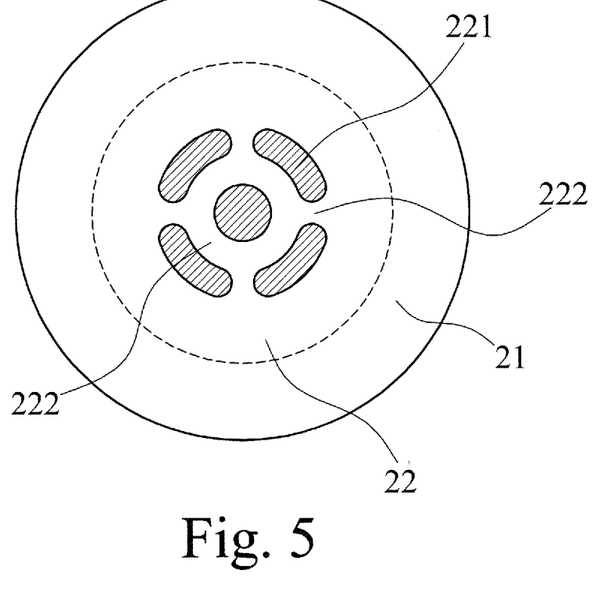
FIG. 5 is a perspective view of a nebulization structure in accordance with the first preferred embodiment of the present invention.
Figure 6:
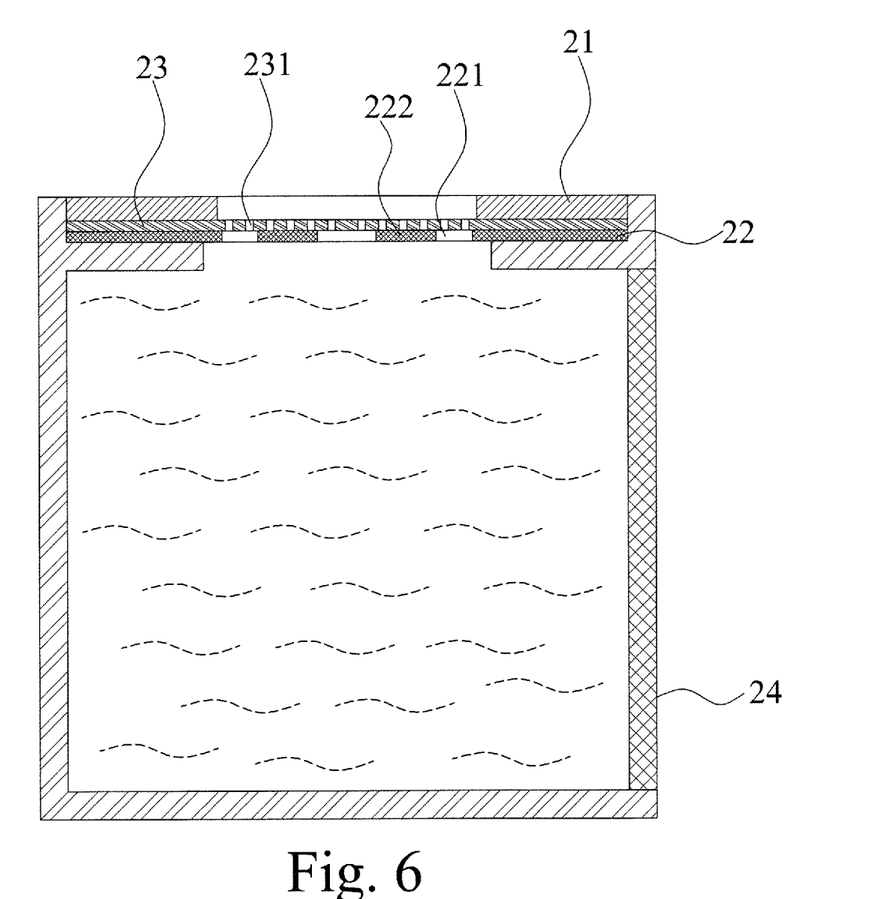
FIG. 6 is a cross-sectional view of a nebulization structure in accordance with the first preferred embodiment of the present invention.
Figure 7:
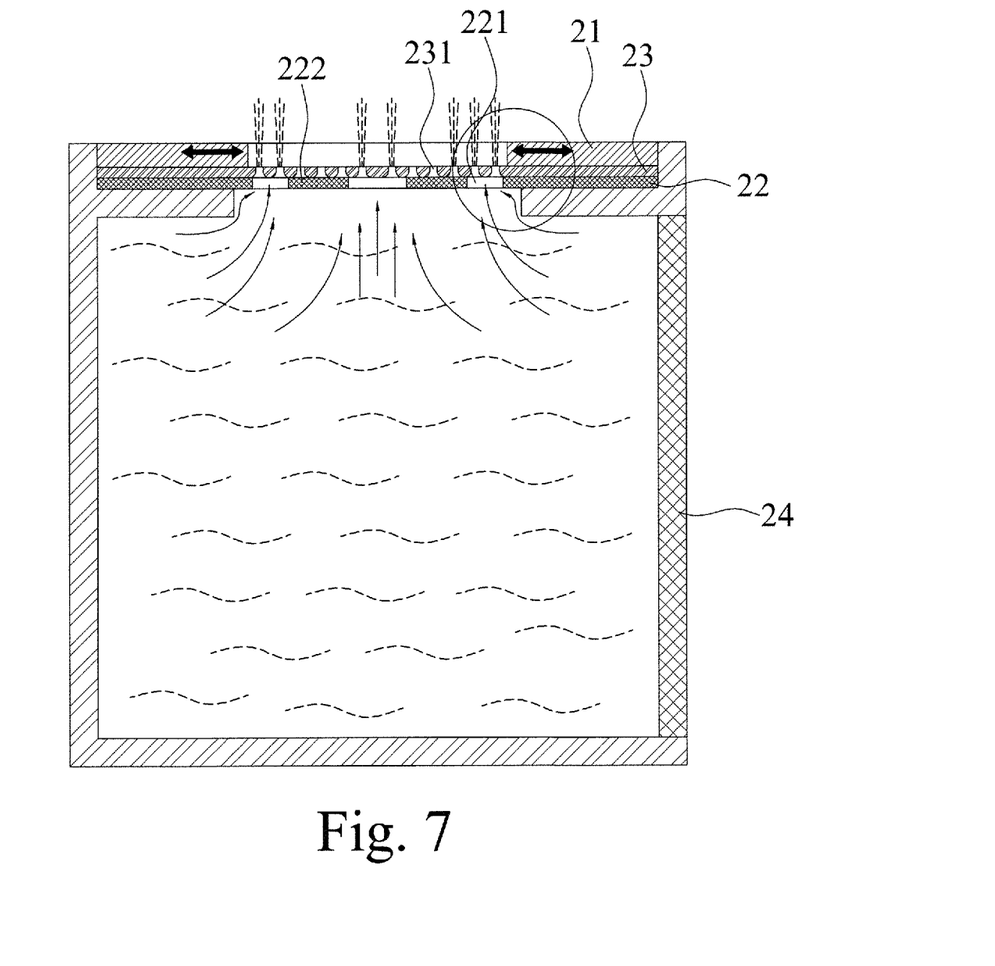
FIG. 7 is a schematic view of an operation of a nebulization structure in accordance with the first preferred embodiment of the present invention.
Figure 8:
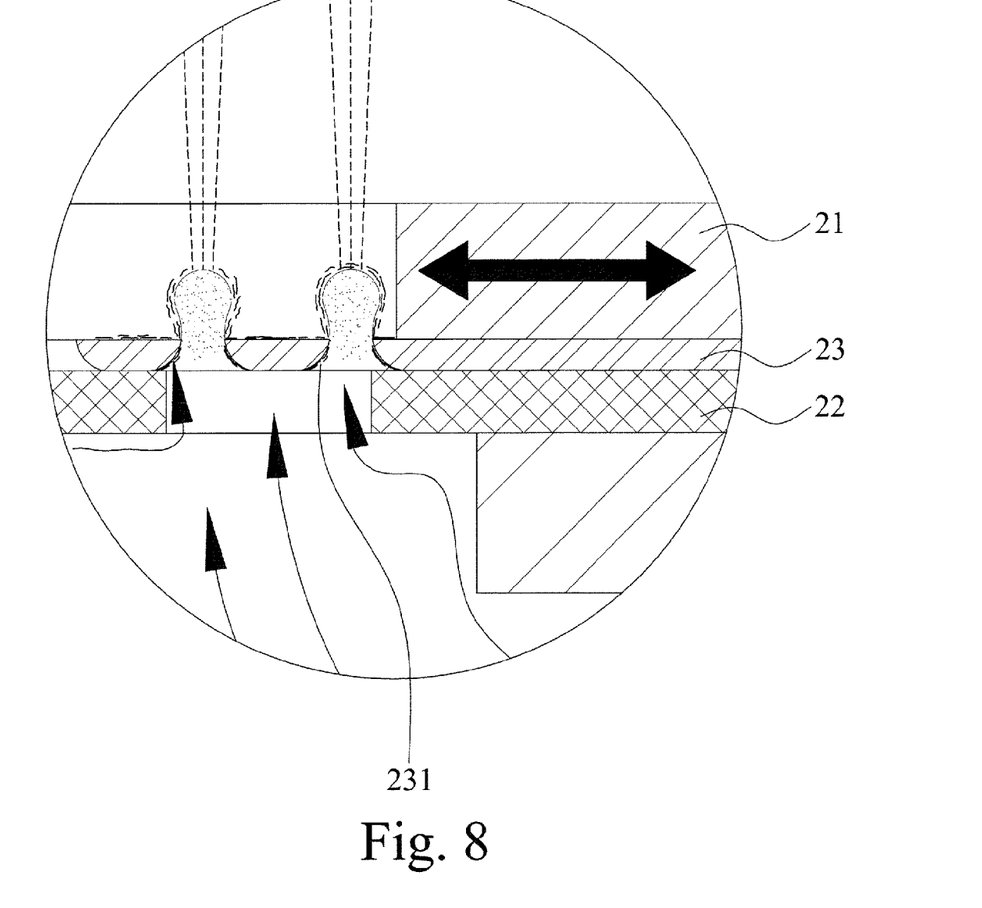
FIG. 8 is a schematic microscopic view of an operation of a nebulization structure in accordance with the first preferred embodiment of the present invention.
Figure 9:
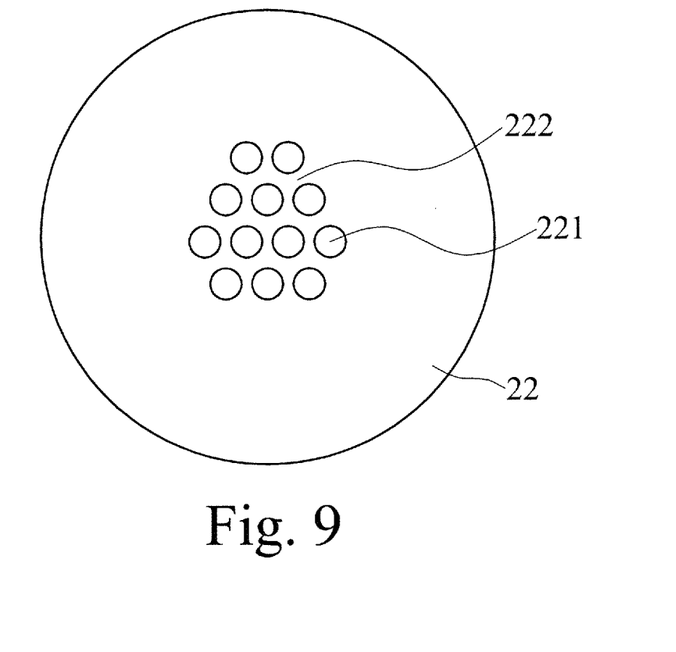
FIG. 9 is a schematic view of another implementation mode of a structure plate of a nebulization structure in accordance with the first preferred embodiment of the present invention.
Figure 10:
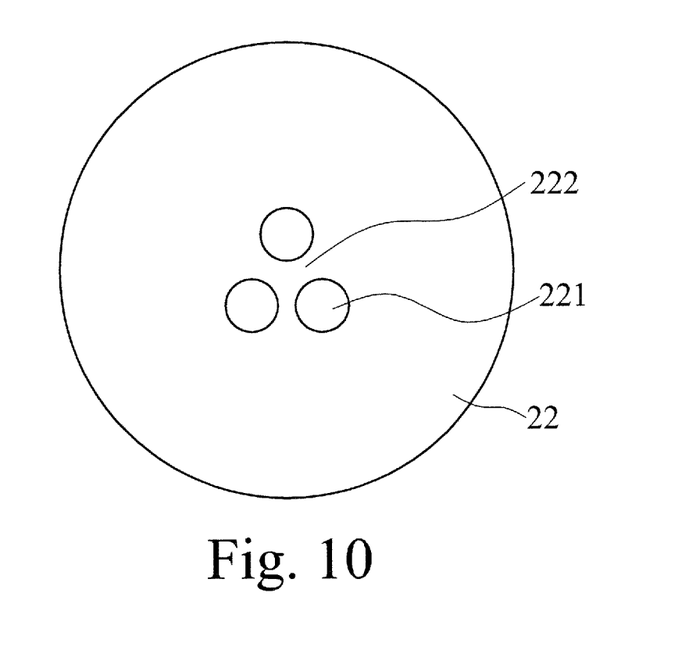
FIG. 10 is a schematic view of another implementation mode of a structure plate of a nebulization structure in accordance with the first preferred embodiment of the present invention.
Figure 11:
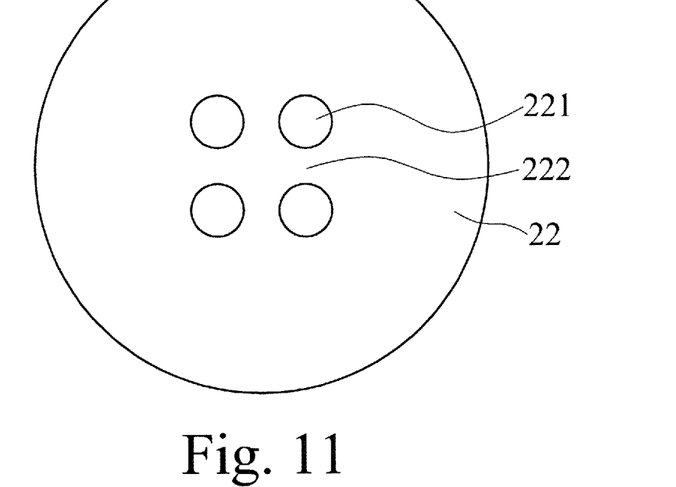
FIG. 11 is a schematic view of another implementation mode of a structure plate of a nebulization structure in accordance with the first preferred embodiment of the present invention.
Figure 12:
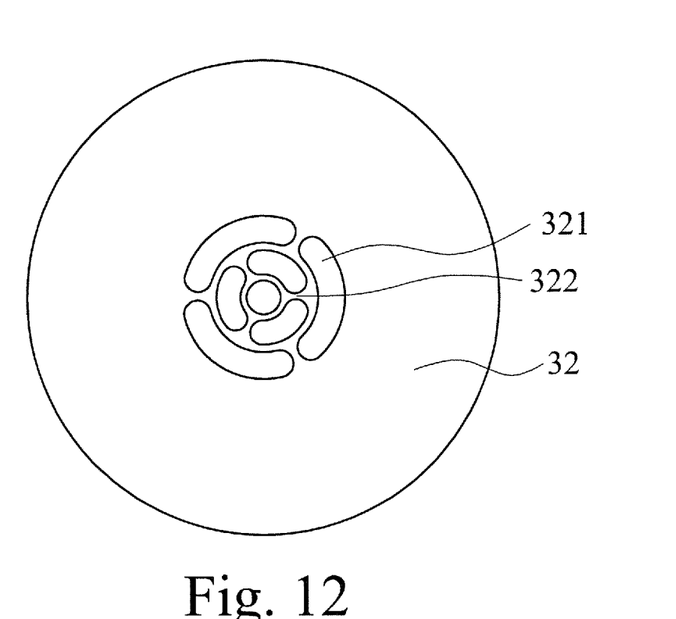
FIG. 12 is a schematic view of another implementation mode of a structure plate of a nebulization structure in accordance with the first preferred embodiment of the present invention.
Figure 13:
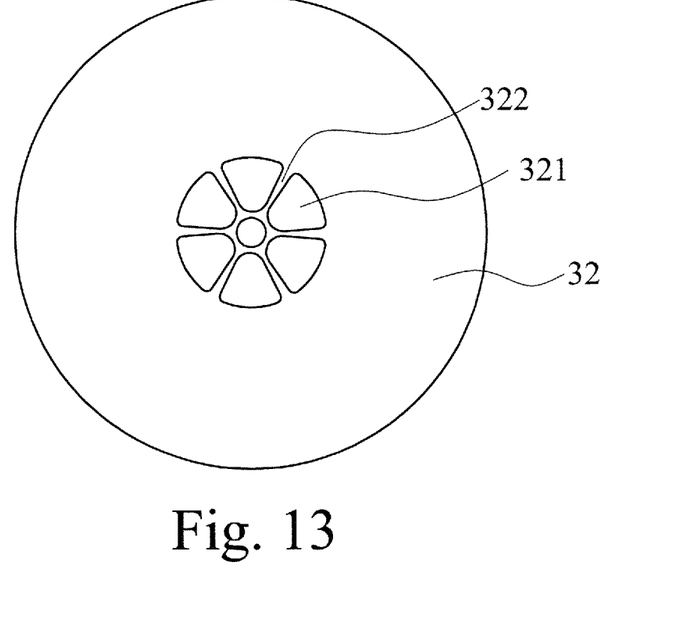
FIG. 13 is a schematic view of another implementation mode of a structure plate of a nebulization structure in accordance with the first preferred embodiment of the present invention.
Figure 14:
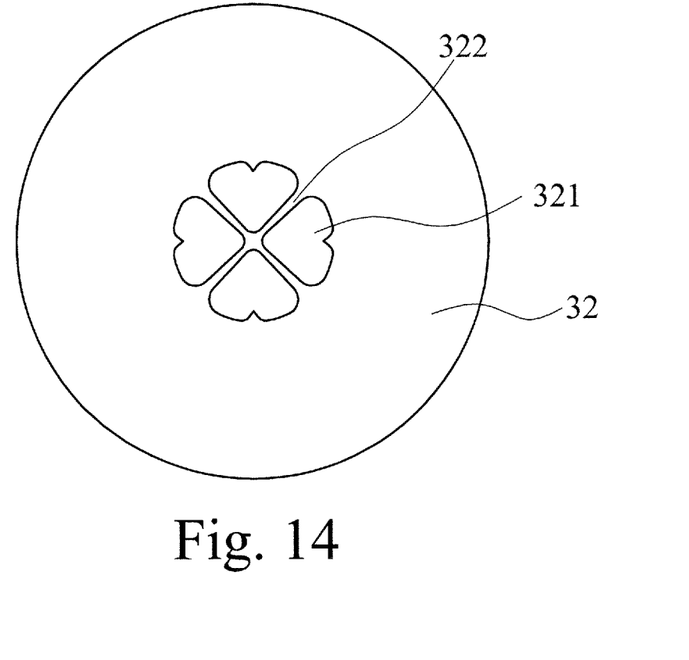
FIG. 14 is a schematic view of another implementation mode of a structure plate of a nebulization structure in accordance with the first preferred embodiment of the present invention.
Figure 15:
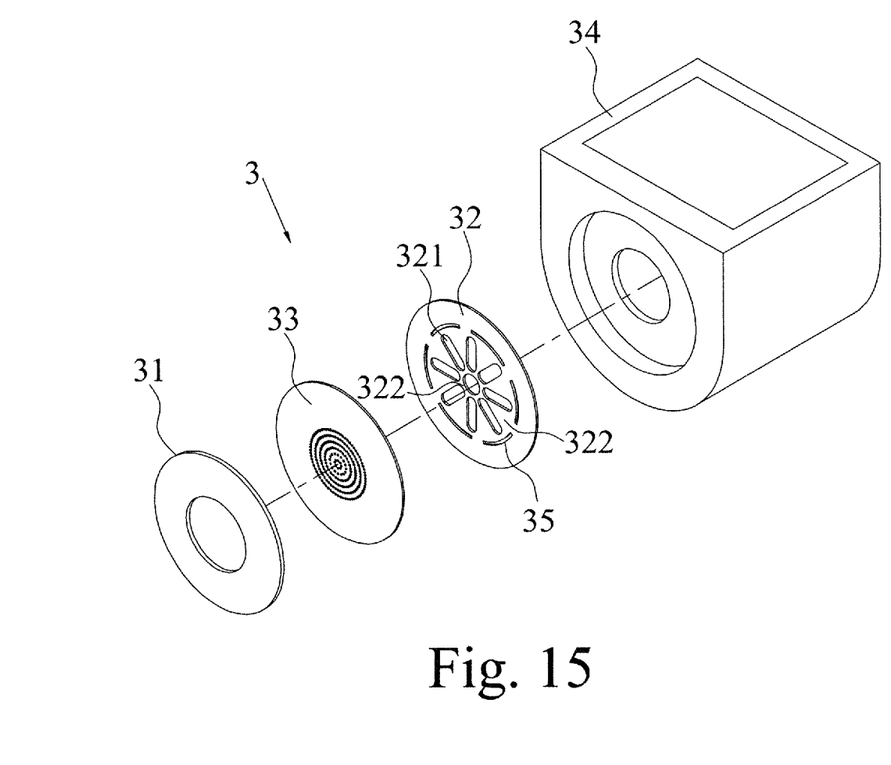
FIG. 15 is an exploded view of a nebulization structure in accordance with a second preferred embodiment of the present invention.
Figure 16:
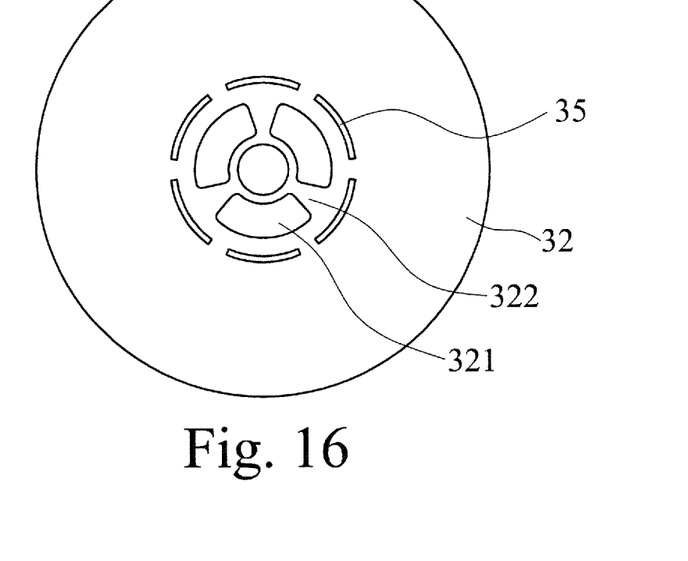
FIG. 16 is a schematic view of another implementation mode of a structure plate of a nebulization structure in accordance with the second preferred embodiment of the present invention.
Figure 17:
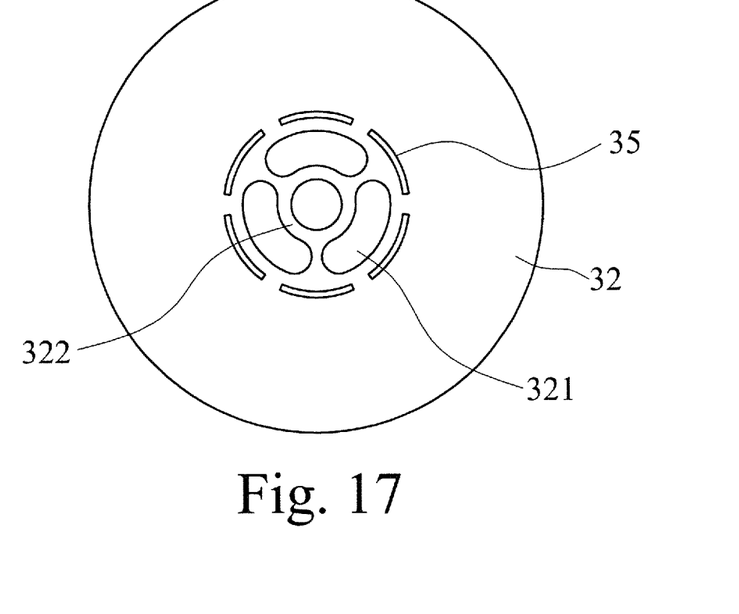
FIG. 17 is a schematic view of another implementation mode of a structure plate of a nebulization structure in accordance with the second preferred embodiment of the present invention.
Figure 18:
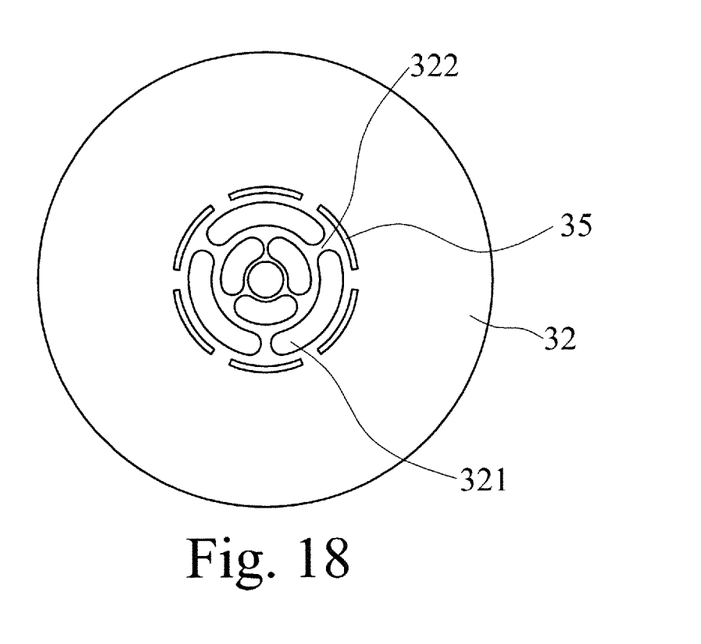
FIG. 18 is a schematic view of another implementation mode of a structure plate of a nebulization structure in accordance with the second preferred embodiment of the present invention.

With reference to FIGS. 4, 5 and 6 for perspective views and a cross-sectional view of a nebulization structure in accordance with the first preferred embodiment of the present invention respectively, the nebulization structure 2 is installed on a side of a cavity 24 and comprises a driving element 21, a structure plate 22 and a nebulization plate 23.

In this preferred embodiment, the driving element 21 is a piezoelectric annular plate made of a piezoelectric ceramic material.

The structure plate 22 is installed on a side of the driving element 21. In this preferred embodiment, the structure plate 22 is in a circular disc shape and includes a plurality of through holes 221, and at least one rib 222 formed between two adjacent through holes. In this preferred embodiment, there are five through holes 221, wherein one of the five through holes 221 is formed at the center position of the structure plate 22, and the other four through holes 221 are arranged radially in a circular shape with respect to the center of the structure plate 22. In this preferred embodiment, the structure plate 22 is preferably made of metal to provide a better effect of transmitting vibration energy. Of course, the material is not limited to metal only, but it also can be a polymer such as polyimide, polyethylene (PE), polypropylene (PP) or polyether ether ketone (PEEK).

The nebulization plate 23 is clamped between the driving element 21 and the structure plate 22 and has a plurality of firing holes 231. In this preferred embodiment, the nebulization When the liquid to be nebulized and the vibration energy are transmitted to the firing holes 231, the high speed produced at the neighborhood of the firing hole 231 makes the inertia force of the nebulized droplets greater than the surface tension of the liquid to be nebulized at the firing holes 231, so that the micro droplets can be sprayed out from the firing holes 231 to achieve a fluid nebulization effect. In addition, due to the thickness of the structure plate, a mini cavity is formed by the through hole on the structure plate so as to reduce of the back pressure of the liquid to be nebulized to improve the nebulization effect.

In other implementation modes, the structure plate 22 has three, four or more through holes, and the through holes 221 are symmetrically and radially arranged with respect to the center of the structure plate 22, and one of the through holes 221 is formed at the center position of the structure plate 22, but the invention is not limited to such arrangement only, but it can also be arranged as shown in FIGS. 9 to 14.

With reference to FIG. 15 for an exploded view of a nebulization structure in accordance with the second preferred embodiment of the present invention, the nebulization structure 3 is installed on a side of a cavity 34 and comprises a driving element 31, a structure plate 32 and a nebulization plate 33. The structure plate 32 has a plurality of through holes 321 formed thereon and at least one rib 322 formed between two adjacent through holes 321.

In this preferred embodiment, the structure and functions of the driving element 31, the rib 322 and the nebulization plate 33 are the same as those of the first preferred embodiment, and thus will not be described. The difference of this preferred embodiment and the first preferred embodiment resides on that the structure plate 32 further includes a plurality of glue overflow passages 35 formed thereon and disposed with an interval apart at the external periphery of the through holes 321 and at positions corresponding to the internal periphery of the piezoelectric element 31. The glue overflow passages 35 are provided for extra glues to overflow therein in order to prevent the extra glues from flowing into the through holes 321 or affecting the nebulization effect.

In other implementation modes, the shape and arrangement of the through holes 321 and the glue overflow passage 35 can be as shown in FIGS. 16 to 18.

In one of the characteristics of the nebulization structure of the present invention, the nebulization plate is made of a polymer material instead, so that the metal nebulization plate can have a better stability and improve the chemical resistance.

In another characteristic of the nebulization structure of the present invention, the rib formed between two adjacent through holes on the structure plate can support the nebulization plate and combine the nebulization plate closely, so that the oscillation frequency of the nebulization plate is close to the vibration frequency of the driving element.

In a further characteristic of the nebulization structure of the present invention, the ribs formed on the structure plate can be used as a passage for transmitting vibration energy and the liquid to be nebulized. Compared with the prior art, the present invention can transmit energy and liquid to be nebulized to the whole area of the nebulization plate more effectively and efficiently, so as to improve the nebulization effect.

What is claimed is:

1. A nebulization structure, comprising:

a container for holding a liquid, and the container further includes a channel for releasing the liquid;

a driving element having an inlet side and an outlet side;

a structure plate, in a circular disc shape, and installed on the inlet side of the driving element, and having four through holes and at least two ribs formed between adjacent two of said four through holes; and a nebulization plate having a plurality of firing holes penetrating the nebulization plate, and the nebulization plate is clamped between the driving element and the structure plate such that the at least two ribs are in contact with and support the nebulization plate and transmit vibration energy from the driving element to the nebulization plate during driving element oscillation, wherein the four through holes are arranged radially with respect to a center point of the structure plate and that the at least two ribs intersect at and overlay the center point of the structure plate, wherein intersection of the at least two ribs are in contact with a center position of the nebulization plate, and the intersection partially covers the channel of the liquid container abuts with some of the plurality of firing holes at the nebulization plate.

2. The nebulization structure of claim 1, wherein the through holes are arranged symmetrically into a circular shape with respect to the center point of the structure plate.

3. The nebulization structure of claim 1, wherein the driving element is a piezoelectric annular plate.

4. The nebulization structure of claim 1, wherein the nebulization plate and the structure plate are coupled and combined by an adhesive.

5. The nebulization structure of claim 1, wherein the nebulization plate is made of a polymer material or a metal material.

6. The nebulization structure of claim 5, wherein the polymer material is one selected from the collection of polyimide, polyethylene (PE), polypropylene (PP) and polyether ether ketone (PEEK).

7. The nebulization structure of claim 1, wherein the structure plate is made of a metal material or a polymer material.

8. The nebulization structure of claim 7, wherein the polymer material is one selected from the collection of polyimide, polyethylene (PE), polypropylene (PP) and polyether ether ketone (PEEK).

9. The nebulization structure of claim 1, wherein the intersection of the at least two ribs does not completely obstruct the liquid from leaving the container.

10. The nebulization structure of claim 1, wherein the intersection of the at least two ribs never seals the channel.

11. A nebulization structure, comprising:

a driving element having an inlet side and an outlet side;

a structure plate, in a circular disc shape, and installed on the inlet side of the driving element, and having four through holes and at least two ribs formed between adjacent two of said four through holes; and a nebulization plate having a plurality of firing holes penetrating the nebulization plate, and the nebulization plate is clamped between the driving element and the structure plate such that the at least two ribs are in contact with and support the nebulization plate and transmit vibration energy from the driving element to the nebulization plate during driving element oscillation, wherein the four through holes are arranged radially with respect to a center point of the structure plate and that the at least two ribs intersect at and overlay the center point of the structure plate, wherein intersection of the at least two ribs are in contact with a center position of the nebulization plate, wherein the nebulization structure is coupled with a container for holding a liquid to be provided to the nebulization structure for nebulization, and the container further includes a liquid-releasing channel overlaid by the structure plate, wherein the intersection of the at least two ribs abuts with some of the plurality of firing holes at the nebulization plate and does not cover the liquid-releasing channel entirely.

12. The nebulization structure of claim 11, wherein the liquid-releasing channel has a first dimension and the intersection has a second dimension, wherein the second dimension is not larger than the first dimension.

13. The nebulization structure of claim 12, wherein the first and second dimensions are cross-sectional areas.

* * * * *